United States Patent [19]

Zeeck et al.

[11] Patent Number: 4,861,775
[45] Date of Patent: Aug. 29, 1989

[54] PHARMACOLOGICAL USE OF PHENOXAZINONES

[75] Inventors: Axel Zeeck, Göttingen; Sabine Breiding-Mack, Döhren; Susanne Grabley, Königstein/Taunus; Hartmut Voelskow, Hattersheim am Main; Gerhard Seibert, Darmstadt, all of Fed. Rep. of Germany

[73] Assignee: Hoechst Aktiengesellschaft, Frankfurt am Main, Fed. Rep. of Germany

[21] Appl. No.: 89,153

[22] Filed: Aug. 25, 1987

[30] Foreign Application Priority Data

Aug. 27, 1986 [DE] Fed. Rep. of Germany ....... 3629062

[51] Int. Cl.$^4$ ............................................. A61K 31/535
[52] U.S. Cl. ................................ 514/229.8; 544/102; 544/104

[58] Field of Search ................ 544/102, 104; 514/232, 514/233, 234, 236, 229.8

[56] References Cited

U.S. PATENT DOCUMENTS 4,667,032  5/1987  Lau et al. ........................ 544/102 X

OTHER PUBLICATIONS

Gerber et al., The Journal of Antibiotics, vol. 36, No. 6, 1983, pp. 688–694.
Berber, Journal of Organic Chemistry, vol. 32, 1967, pp. 4055–4057.

*Primary Examiner*—Richard L. Raymond
*Attorney, Agent, or Firm*—Finnegan, Henderson, Farabow, Garrett, & Dunner

[57] ABSTRACT

Streptomyces spec. DSM 3813 produces novel compounds with a basic phenoxazinone structure, which have an antifungal and antiviral action and can be used as lipoxygenase inhibitors.

4 Claims, No Drawings

PHARMACOLOGICAL USE OF PHENOXAZINONES

A microorganism strain which has been identified as Streptomyces spec. has been isolated from a soil sample and deposited in the Deutsche Sammlung von Mikroorganismen (DSM) (German Collection of Microorganisms) under number DSM 3813.

This strain is characterized as follows

| | |
|---|---|
| Spore surface: | Sm |
| Spore morphology: | Rf |
| Chromogenicity: | M+ |
| Air mycelium color: | gray |

In a nutrient solution containing a carbon and nitrogen source and the usual inorganic salts, the strain DSM 3813 produces novel compounds with a basic phenoxazinone structure. These compounds are thus obtainable by fermentation of the strain DSM 3813 and isolation from the mycelium, and in particular from the fermentation medium.

It is indeed known from publications that Actinomycetes can synthesize an aminophenoxazinone [Gerber et al.: J. Antibiot., page 688 (1983); and Gerber, N.N.: J. Org. Chem. 32, 4055 (1967)]. However, the microbiologically obtained phenoxazinones described below are novel.

The novel phenoxazinones have an antifungal and antiviral action and act as an anthelmintic and as inhibitors of lipoxygenase, and can therefore be used in the form of pharmaceutical preparations for the treatment of humans and animals and in the diagnostic field.

The novel compounds can also be used as intermediates for the preparation of novel derivatives with a comparable action.

The invention thus relates to:
1. The compound of the general formula I

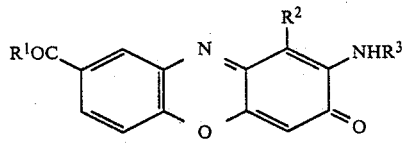

in which
$R^1$ denotes hydroxyl or ($C_1$-$C_5$)-alkoxy or amino,
$R^2$ denotes hydrogen or the group of the general formula

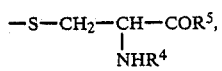

with $R^4$ as hydrogen or ($C_1$-$C_5$)-acyl
and $R^5$ as hydroxyl or ($C_1$-$C_5$)-alkoxy,
and
$R^3$ denotes hydrogen or ($C_1$-$C_5$)-acyl.

2. A process for the preparation of the compounds of the general formula I, which comprises
   (a) culturing Streptomyces spec. DMS 3813 on a nutrient medium until the compounds of the general formula I in which
      (1) $R^1$ denotes hydroxyl, $R^2$ denotes

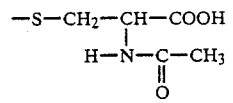

and $R^3$ denotes hydrogen, or
      (2) $R^1$ denotes hydroxyl, $R^2$ denotes hydrogen and $R^3$ denotes acetyl, or
      (3) $R^1$ denotes amino and $R^2$ and $R^3$ denote hydrogen, accumulate in the nutrient medium and if appropriate
   (b) isolating the compounds mentioned and forming derivatives.
3. The use of the compounds mentioned of the general formula I for the preparation of medicines or diagnostics.

The invention is illustrated in detail and defined in the patent claims below.

The compounds of the general formula I in which
(a) $R^1$ denotes hydroxyl, $R^2$ denotes

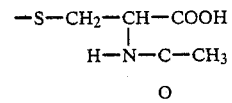

and $R^3$ denotes hydrogen, or
(b) $R^1$ denotes hydroxyl, $R^2$ denotes hydrogen and $R^3$ denotes acetyl, or
(c) $R^1$ denotes amino and $R^2$ and $R^3$ denote hydrogen, can be prepared fermentatively with the aid of Streptomyces spec. DSM 3813.

Instead of the strain DSM 3813, its mutants and variants can of course also be employed, if they produce the compound mentioned. Such mutants can be generated in a manner which is known per se by physical means, for example irradiation, such as with ultraviolet rays or X-rays, or by chemical mutagens, such as, for example, ethanesulfonic acid methyl ester (ethylmethylsulfonate, EMS) or 2-hydroxy-4-methoxy-benzophenone (MOB).

Assimilable carbohydrates and sugar alcohols, such as glucose, lactose or D-manoitol, and natural products containing carbohydrates, such as malt extracts, are suitable preferred sources of carbon for the aerobic fermentation. Possible nitrogen-containing nutrients are: amino acids, proteins and their degradation products, such as peptones or tryptones, and furthermore meat extracts, ground seeds, for example from maize, wheat, beans, soya or cotton plants, distillation residues from the production of alcohol, meat meals or yeast extracts, and also ammonium salts and nitrates. Other inorganic salts which the nutrient solution can contain are, for example, chlorides, carbonates, sulfates or phosphates of the alkali or alkaline earth metals, iron, zinc and manganese.

The formation of the compounds Ia, b and c which can be prepared by fermentation proceeds particularly well in a nutrient solution containing about 2% of soya flour and 2% of mannitol, in each case based on the total weight of the nutrient solution.

The fermentation proceeds aerobically, that is to say, for example, in a submerse culture with shaking or stirring in shaking flasks or fermenters, if appropriate with the introduction of air or oxygen. The fermentation can be carried out in a temperature range from about 18° to 35° C., preferably at about 25° to 30° C., in particular at 28° to 30° C. Fermentation is carried out in a pH range between 5 and 8.5, preferably between 5.5 and 8.0. Under these conditions, the culture broth in general shows a noticeable accumulation of the compounds Ia, b and c after 2 to 6 days.

Culturing is preferably carried out in several stages, that is to say one or more precultures are first prepared in a liquid nutrient medium and are then transinoculated into the actual production medium, the main culture, for example in a volume ratio of 1:10. The preculture is obtained, for example, by transinoculating a sporulated mycelium into a nutrient solution and allowing it to grow for about 48 to 72 hours. The sporulated mycelium can be obtained by allowing the strain to grow on a solid or liquid nutrient medium, for example yeast-/malt agar, for about 7 days.

The course of the fermentation can be monitored with the aid of the pH of the culture or with the aid of the mycelium volume by thin-layer chromatography. The compounds Ia, b and c which can be prepared by fermentation are isolated from the culture by known methods, taking into account the chemical, physical and biological properties of the products.

It is appropriate first to carry out detection by thin-layer chromatography on silica gel with a polar solvent or solvent mixture, for example n-butanol/acetic acid/water, as the mobile phase.

The compounds can be extracted from the non-filtered culture broth with an organic solvent which is water-immiscible or only slightly miscible with water, such as n-butanol, acetone, methanol and the like, advantageously at pH 5 to 6. Alternatively, the lyophilized culture can be extracted with methanol or other lower alkanols in order to isolate the compounds in crude form.

Colored extracts are obtained, from which, after the lipophilic constituents have been removed, 3 fractions are obtained by extraction with corresponding solvents, for example with a mixture of chloroform/petroleum ether, and separation of the crude product by chromatography.

To isolate the individual fractions from the degreased crude extract, this is advantageously purified over hydroxyalkoxypropyldextran (®Sephadex LH brands), for which mixtures of lower alkanols and water, for example methanol and water in a volume ratio of 9:1, or pure methanol have proved suitable mobile phases. The components adsorbed in the form of zones of different color are isolated in succession in the form of eluates of different color, in each of which one of the components is highly concentrated.

The usual process steps, such as chromatography or renewed gel filtration in suitable organic solvents, can be used to isolate the pure compounds. Chromatography on Sephadex LH brands has proved particularly suitable, pure methanol or methanol/$H_2O$ in a ratio of 9:1 to 90:1 being used in particular as the mobile phase.

The pure compounds Ia, b and c are amorphous to crystalline solids without pH indicator properties. The compounds are readily soluble in strongly polar solvents, such as methanol, dimethylsulfoxide and water, and moderately soluble in ethanol, chloroform and methylene chloride. They are insoluble in alkanes and acetone.

Conversion into the derivatives of the compounds Ia, b and c is carried out in a manner which is known per se. For example, Ia and Ib can be converted into the esters by methanolysis in the presence of strong acids. Mixtures of methanol and anhydrous hydrochloric acid in which the methanolysis proceeds completely in the course of 1 hour to 24 hours at temperatures of 20° to 60° C., in particular at room temperature, are suitable examples.

The acetyl radical is split off from Ia in a manner which is known per se, preferably by means of aminoacylases in an aqueous medium.

The pharmacological action of the compounds against viruses, for example against vaccina P71 in hela cells and influenza A in vero cells, and against protozoa, such as Trichomonas vaginalis, and fungi, such as Candida albicans, is of particular interest. The products can also advantageously be used as an anthelmintic. They are particularly active against a large number of helminths, for example Hemonchus, Trichostrongylus, Ostertagla, Cooperia, Chabertia, Strongyloides, Oesophagostomum, Hyostrongylus, Ancylostoma, Ascaris and Heterakis. The activity against gastrointestinal Strongylides and lung worms which affect above all domestic and useful animals is particularly pronounced. The compounds according to the invention are therefore used in particular in veterinary medicaments.

The substances are stable in the solid state and in solutions in the pH range from 2 to 8, in particular from 5 to 8. The compounds can thus be incorporated into the usual galenical formulations.

The invention is illustrated in more detail in the following examples. Percentage data relate to the weight, unless indicated otherwise. Mixing ratios in liquids relate to the volume, if no other details are given.

EXAMPLE 1

(a) Preparation of a spore suspension of the producer strain Streptomyces spec. DSM 3813

Several slant tubes with oat flakes agar are inoculated with DSM 3813 and incubated at 30° C. for about 6 days. The oat flakes agar is prepared as follows: 20 g of oat flakes are boiled in 1 liter of water for 20 minutes and the mixture is then filtered. 18 g of agar and 2.5 ml of a trace element solution (3 g of $CaCl_2 \cdot 2H_2O$, 1 g of Fe-III citrate, 0.2 g of $MnSO_4$, 0.1 g of $ZnCl_2$, 0.025 g of $CuSO_4.5H_2O$, 0.02 g of $Na_2B_4O_7 \cdot 10H_2O$, 0.004 g of $CaCl_2$ and 0.1 g of $Na_2M_6O_4 \cdot H_2O$ dissolved in 1 liter of distilled water) are added to the filtrate. Before sterilization, the pH is brought to 7.8.

The spores of each individual tube are floated off with 3 ml of liquid [0.9% of NaCl and 0.1% of polyoxyethylene sorbitan monooleate (®Tween 80) in distilled water]. The suspensions are combined and stored at 4° C. until the main culture is inoculated.

(b) Preparation of a preculture of the producer strain DSM 3813 in a conical flask 5 conical flasks (300 ml capacity) each containing 100 ml of nutrient solution (40 g of glucose, 30 g of soya flour, 2.5 g of NaCl and 2.5 g of $CaCO_3$ per liter of distilled water, brought to pH 7.5 before sterilization) are inoculated with in each case 1.5 ml of the freshest possible spore suspension and are incubated on a shaking machine 5 (180 revolutions per minute) at 30° C. for 72 hours.

(c) Preparation of the compounds Ia, b and c with a culture of the producer strain DSM 3813

A 300 ml conical flask with 100 ml of nutrient solution (20 g of soya flour and 20 g of mannitol per liter of distilled water, brought to pH 7.5 before sterilization) is inoculated with 3 ml of the preculture and incubated at 30° C. on a shaking machine (180 revolutions per minute). The production maximum is reached after about 96 to 120 hours. The total yields of compounds Ia, b and c are about 200 mg/liter.

EXAMPLE 2

Preparation of a culture of the producer strain DSM 3813 in a fermenter

A fermenter with a capacity of 13 liters is operated under the following conditions: 10 liters of air per minute are introduced into the culture liquid (medium as in Example 1c) at an incubation temperature of 30° C. and at 600 revolutions per minute of the stirrer. The fermenter is inoculated with 500 ml of the preculture (see 1b). The production optimum is reached after about 96 to 120 hours. The total yields of the compounds Ia, b and c are about 400 mg/liter.

EXAMPLE 3

Isolation of the compounds Ia, b and c 60 g of lyophilisate from 4 liters of culture filtrate of the strain DSM 3813 are extracted 3 times with 1 liter of methanol at pH 5 to 6 and the extracts are evaporated in vacuo. The residue is taken up in methanol/water (9:1, v:v) and the mixture is chromatographed in several portions on ®Sephadex LH 20 with methanol/water 9:1. The compounds Ib and Ia are first eluted together as a drawn-out yellow- to red-brown zone and are then followed by the compound Ic as a brown-red zone. The fractions Ia and Ib obtained from several separations on Sephadex are chromatographed again on Sephadex LH 20 with methanol, Ib being eluted before Ia. A large proportion of Ib remains undissolved when the mixture is dissolved, and is filtered off. A total of 70 mg of red amorphous Ia and 14 mg of yellow, partly crystalline Ib is obtained. The fractions containing Ic are separated again on 2 preparative silica gel thick-layer plates (20×20 cm) in the system ethyl acetate/methanol/water 6:2:1. The orange-red main zone is eluted with chloroform/methanol 1:1, so that further purification on Sephadex LH 20 with analytical grade methanol gives 7.5 mg of Ic.

EXAMPLE 4

Preparation of the methyl ester from the compound Ib 20 ml of freshly prepared 5 molar methanolic hydrochloric acid are added to 10 mg of Ib and the mixture is stirred at room temperature for 24 hours. The solution is evaporated in vacuo and the residue is chromatographed on Sephadex LH 20 with methanol/chloroform 9:1 to give 5.5 mg of Ib methyl ester.

EXAMPLE 5

Preparation of the methyl ester from the compound Ia 15 ml of freshly prepared 5 molar methanolic hydrochloric acid are added to 50 mg of Ia and the mixture is stirred at room temperature for 24 hours. After evaporation in vacuo, the residue is chromatographed on Sephadex LH 20 (column 2.5×40 cm) with methanol to give 29 mg of Ia dimethyl ester.

Spectroscopic data of the compounds Ia, b and c:

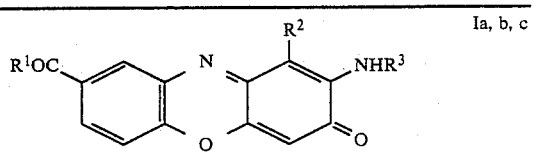

| Compound | R$^1$ | Groups R$^2$ | R$^3$ |
|---|---|---|---|
| Ia | OH | —S—CH$_2$—CH(HN—O—C(=O)—CH$_3$)—COOH | H |
| Ib | OH | H | —OOC—CH$_3$ |
| Ic | —NH$_2$ | H | H |

| | Ia | Ib | Ic |
|---|---|---|---|
| UV[nm] | 428 | 402 | 429 |
| | 254 | 250 | 256 |
| IR[cm$^{-1}$] | 3390 | 3425 | 3420 |
| (KBr) | 3305 | 3295s | 3325 |
| | 1725w | | |
| | 1692m | 1687m | |
| | 1640m | 1618s | |
| | 1580 | 1588 | 1590s |
| | | | 1555 |
| | | 1510s | 1562 |
| | | | 1393s |

Ia:
$^1$H-NMR 200 MHz, d$_6$-DMSO
=1.80 (s, 3H); 3.17 (d, 2H); 4.35 (dd, 1H); 6.48 (s, 1H); 7.22 (broad, NH$_2$); 7.63 (d, 1H); 8.04 (dd, 1H); 8.25 (d, NH); 8.30 (d, 1H) ppm $^{13}$C-NMR: 50 MHz, CD$_3$OD
=22.9 (CH$_3$); 37.5 (CH$_2$); 56.6 (CH); 102.1 (C-1); 105.0 (C-4); 116.2 (C-6); 130.7; 131.9 (C-7, C-9); 134 (C-9a); 136.3 (C-8); 144.9 (C-5a); 147.8 (C-10a); 151.2 (C-4a); 152.2 (C-2); 173.0; 173.6 (C-4', C-5'); 177.1 (C-3); 180.5 (C-1') ppm Ib:
$^1$H-NMR: 200 MHz, 60° C., d$_6$-DMSO
=2.25 (s, 3H); 6.52 (s, 1H); 7.57 (d, 1H); 8.16 (dd, 1H); 8.31 (s, 1H); 8.32 (d, 1H); 9.65 (1H, NH) ppm $^{13}$C-NMR: 50 MHz, 60° C., d$_6$-DMSO
=24.1 (CH$_3$); 103.9; 113.0; 115.4; 129.8; 132.1; 132.7; 137.5; 144.5; 148.4; 148.9; 166.0; 170.2; 179.2 ppm

EXAMPLE 6

Anthelmintic action of the compound Ia

The anthelmintic action of the ammonium salts of the compound Ia is investigated on lambs with a body weight of 30–40 kg. For this, the lambs are artificially infected with infection stages of fourth stomach (Haemunchus contortus) and small intestine (Trichostrongylus colubriformis) nematodes. At the end of the development period (prepatency period) of the nematodes, Ia is administered in a dosage of 2.5 mg/kg (subcutaneously).

The percentage reduction in sheep nematodes is determined by coproscopic investigations before and up to 14 days after administration and subsequent autopsy with helminthological working up. An 80 to 90 % reduction can be detected.

We claim:
1. A method for the treatment of an animal for fungal, protozoa, viral and anthelmintic infections which com- prises administering to said animal an amount effective for said treatment of a compound of formula

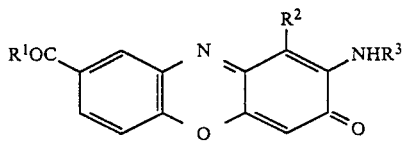

in which
R[1] is hydroxyl or $(C_1-C_5)$-alkoxy or amino,
R[2] is hydrogen or the group of the formula

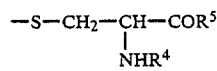

wherein $R^4$ is hydrogen or $(C_1-C_5)$-acyl
and $R_5$ is hydroxyl or $(C_1-C_5)$-alkoxy,
and
$R^3$ is hydrogen or $(C_1-C_5)$-acyl.

2. The method as claimed in claim 1 wherein said animal is a human being.

3. A method for the treatment of an animal for fungal, protozoa, viral and anthelmintic infections which comprises administering to said animal a pharmaceutical composition comprising an amount effective for said treatment of a compound of formula I

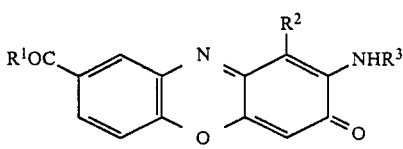

in which
$R^1$ is hydroxyl or $(C_1-C_5)$-alkoxy or amino,
$R^2$ is hydrogen or the group of the formula

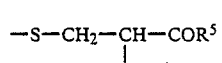

wherein $R^4$ is hydrogen or $(C_1-C_5)$-acyl
and $R^5$ is hydroxyl or $(C_1-C_5)$-alkoxy,
and
$R^3$ is hydrogen or $(C_1-C_5)$-acyl, together with a pharmaceutically acceptable carrier.

4. The method as claimed in claim 3 wherein said animal is a human being.

* * * * *